United States Patent [19]

Otomo

[11] Patent Number: 5,575,105
[45] Date of Patent: Nov. 19, 1996

[54] TERMITE ALARM UNIT

[75] Inventor: Hirotaka Otomo, Tokyo, Japan

[73] Assignee: Cats, Inc., Tokyo, Japan

[21] Appl. No.: 335,404

[22] Filed: Nov. 3, 1994

[30] Foreign Application Priority Data

Jun. 29, 1994 [JP] Japan .................. 6-170134

[51] Int. Cl.⁶ ............................................. A01M 1/20
[52] U.S. Cl. .................... 43/132.1; 73/587; 340/573; 43/124
[58] Field of Search ...................... 43/124, 132.1; 73/587; 340/573, 541, 552, 561

[56] References Cited

U.S. PATENT DOCUMENTS

| | | | |
|---|---|---|---|
| 2,126,664 | 8/1938 | Reis | 43/124 |
| 4,277,907 | 7/1981 | Ernest | 43/131 |
| 4,671,114 | 6/1987 | Litzkow | 73/587 |
| 4,794,549 | 12/1988 | Van Albert | 340/573 |
| 4,809,554 | 3/1989 | Shade | 73/587 |
| 4,862,145 | 8/1989 | Meehan | 340/573 |
| 4,884,064 | 11/1989 | Meehan | 340/573 |
| 4,941,356 | 7/1990 | Pallaske | 73/587 |
| 4,945,673 | 8/1990 | Lavelle | 43/124 |
| 5,329,726 | 7/1994 | Thorne | 43/124 |

FOREIGN PATENT DOCUMENTS

| | | | |
|---|---|---|---|
| 4326019 | 2/1995 | Germany | 43/124 |
| 0683697 | 9/1979 | U.S.S.R. | 340/561 |

Primary Examiner—Joseph J. Hail, III
Assistant Examiner—James Miner
Attorney, Agent, or Firm—Wenderoth, Lind & Ponack

[57] ABSTRACT

A cellulose-containing member is provided with a plurality of holes transversely extending therethrough. An emitting element and a receiving element are located at opposite ends, respectively, of each of the holes. The presence or absence of termites is detected by the obstruction of an output wave from the emitting element caused by termites invading the holes, whereupon a detection signal is generated to cause alarm lamps and so on to light up for alarm display. Simultaneously, in order to estimate the number of invading termites, the number of occurences of an obstruction by the termites of the output waves from the emitting elements is counted.

15 Claims, 5 Drawing Sheets

FIG. I 5,575,105

TERMITE ALARM UNIT

BACKGROUND OF THE INVENTION

1. Field of the Invention

The present invention relates to a termite alarm unit capable of constantly watching for termites or white ants which may eat woody parts of a house and providing an external indication of the invasion thereof.

2. Description of the Related Art

Up to now, the invasion of termites into a house has been visually inspected by an investigator, who does not crawl under the floor of the house until a request for investigation is made by the owner of the house.

Although the termites are often detected upon the investigation requested by the owner of house, the detection will be unfortunately too late. Namely, a request for the investigation is not made until winged ants appear or termites are seen by accident, whereupon the house has been already heavily eaten by the termites so as to replacement of a part of the house.

For this reason, the investigation should be frequently carried out by the investigator, but such is costly or actually impossible to carry out due to insufficient investigators.

SUMMARY OF THE INVENTION

It is, therefore, the object of the present invention to provide a unit capable of constantly watching for and detecting termites.

According to an aspect of the present invention, there is provided a termite alarm unit comprising a sensor section composed of a cellulose-containing member including a plurality of transversely extending through holes each hole having one opening end provided with an emitting element and having the other opening end provided with a receiving element;

a judgment section for detecting the invasion of termites to provide an output signal, in response to the obstruction of an output wave from the emitting element to be received by the corresponding receiving element; and an alarm display section for issuing an alarm, in response to the output signal provided from the judgment section.

Such a termite alarm unit may include a counter section for counting up the number of output signals sent out from the judgment section to provide its output to an alarm display serving to generate an alarm whenever counting one or several termites.

The cellulose-containing member is protected by a cover whose bottom is open. The cellulose-containing member may be made of a lumber or a hardened pulp, and may have legs to be fixedly inserted into the ground.

The sensor section is preferably composed of an emitting element and a receiving element, for example, an infrared ray emitting element and an infrared ray receiving element corresponding thereto, or an ultrasonic wave emitting element and a corresponding ultrasonic wave receiving element, to thereby ensure that an output wave transmitted between the two elements can be obstructed by termites.

Accordingly, the sensor section is disposed on the ground surface, and the judgment section judges that termites have invaded if an output wave from the emitting element to the receiving element is obstructed by the passage of the termites through the holes, to issue a judgment output allowing an external alarm display section to display the judgment.

The results of judgment by the judgment section may be counted and, after a predetermined count, may cause an output of the alarm display section.

Thus, the termite alarm unit of the present invention is capable of always watching for the invasion of termites and detecting instantly the invasion thereof. The counter section, if provided, displays the number of occurrences of the detected invasion, enabling the termites to be quantitatively estimated based on its frequency.

The cellulose-containing member may be covered by a cover so as to advantageously protect the sensor section.

A lumber, if used as the cellulose-containing member, will be easy to obtain and easy to manufacture. Also, a hardened pulp will ensure ease of molding.

Further, by providing the cellulose-containing member with legs and inserting the legs into the ground, the sensor section can be prevented from being raised from the ground or being displaced.

BRIEF DESCRIPTION OF THE DRAWINGS

Many other advantages, features and objects of the present invention will be understood by those of ordinary skill in the art referring to the attached drawings, which illustrate a preferred embodiment of the present invention, and in which.

DETAILED DESCRIPTION OF THE PREFERRED EMBODIMENT

An embodiment of the present invention will now be described with reference to the accompanying drawings.

Figure 1:
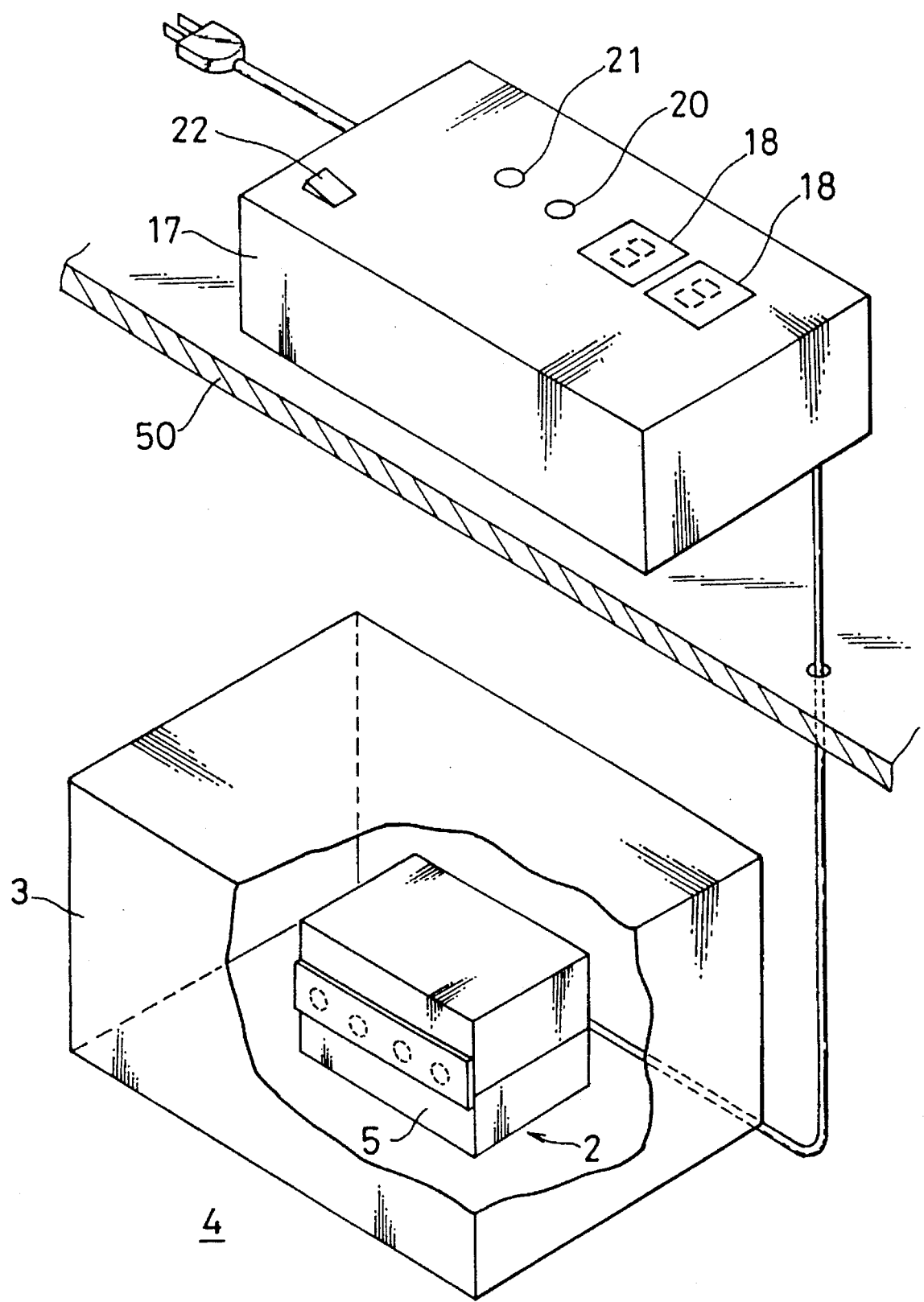
FIG. 1 is a schematic external view of a termite alarm unit in accordance with the present invention.
Figure 2:
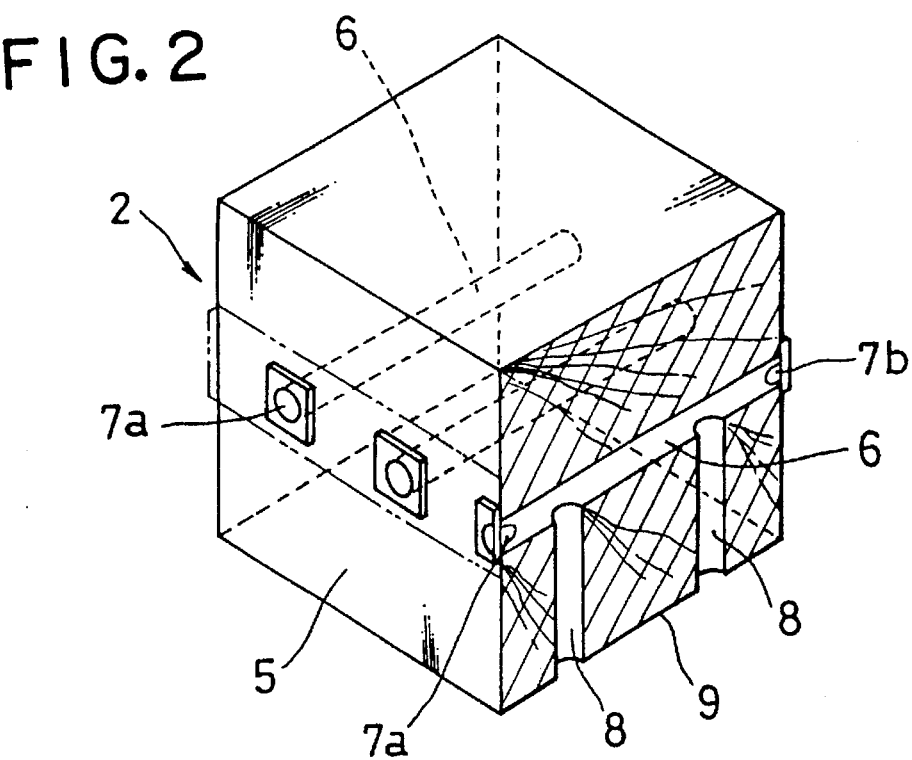
FIG. 2 is a partially cut-away perspective view showing a sensor section of the termite alarm unit in accordance with the present invention.
Figure 3:
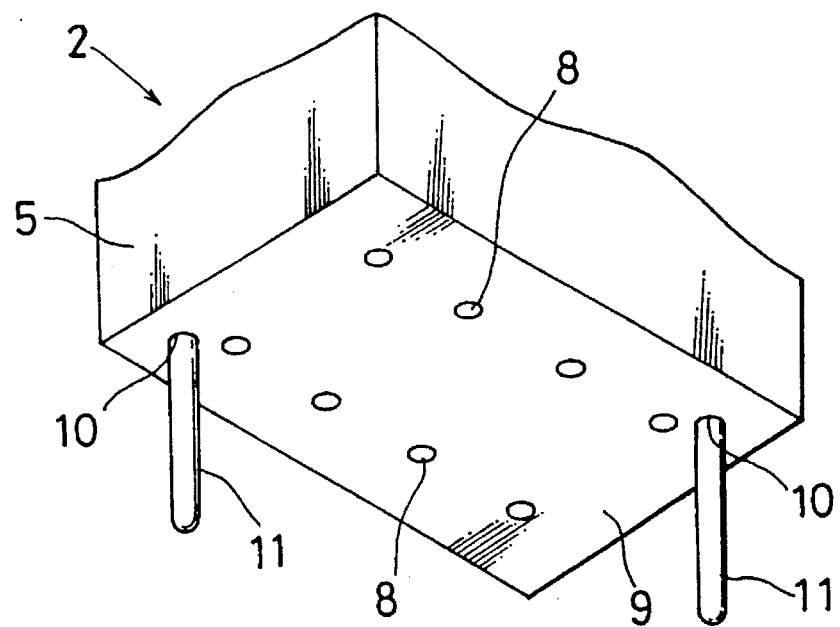
FIG. 3 is a perspective view of the sensor section, viewed from below, of the termite alarm unit in accordance with the present invention.

FIGS. 1 to 3 diagrammatically depict the present invention, in which a termite alarm unit generally designated at 1 comprises a judgment section 15 and an alarm display section 16 enclosed in a case 17 disposed on a floor 50 of a house, and a sensor section 2 protected by a cover 3 placed on the ground surface 4 under the floor 50.

The sensor section 2 is made of a lumber, in particular, a pine wood. Without being limited to it, however, the sensor section 2 can be a member 5 containing cellulose that, for example, may be fashioned from a hardened pulp. The sensor section 2 is preferably in the shape of a cube or rectangular parallelepiped.

The cellulose-containing member 5 has a plurality of through holes 6 transversely extending therethrough, the opposite open ends of each of the through holes 6 being provided with an infrared ray emitting element 7a and an infrared ray receiving element 7b so as to constantly allow the infrared rays to be irradiated from the emitting element 7a to the receiving element 7b. The through holes 6 are connected to a plurality of holes 8 vertically extending to the underside 9 of the member 5 to define therein a plurality of openings that are in turn in contact with the ground surface 4. The member 5 may be slightly sunk into the ground. As is clear from FIG. 3, the underside 9, in particular, has not only the vertically extending holes 8 but also leg mounting holes 10 into which are fitted legs 11 intended to be inserted into the ground upon the installment of the sensor section 2 on the ground surface 4, thereby preventing the sensor section 2 from being raised.

The case 17 comprises on its top surface the alarm display section including two numerical displays 18 for numerically displaying the number of occurrences of the detected invasion of termites; two display lamps 20 and 21 for chromatically displaying whether a termite has invaded or not, the lamp 20 in blue lighting up in the absence of the invasion by the termites, the lamp 22 in red lighting up in the presence thereof; and a reset switch 22.

Figure 4:
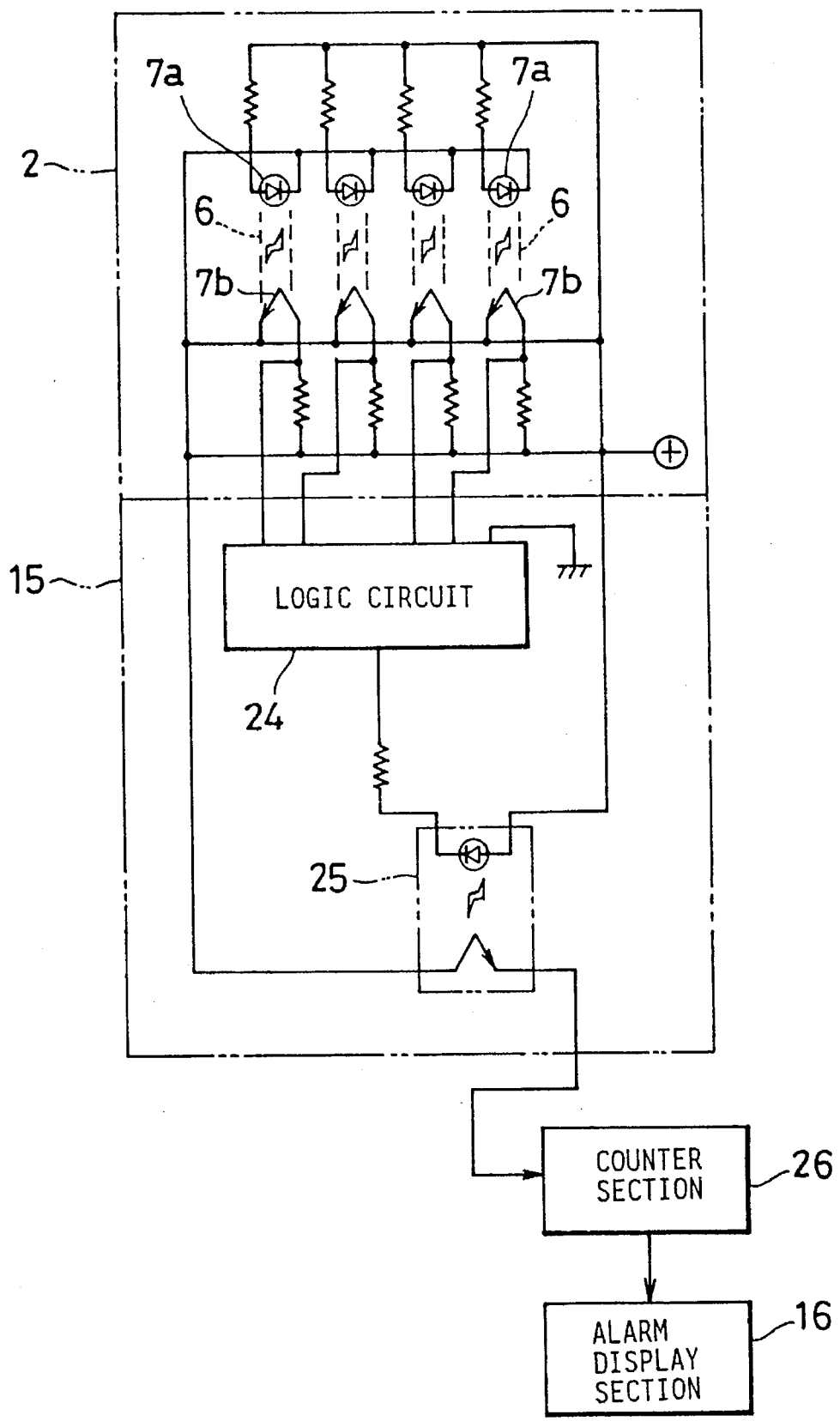
FIG. 4 schematically depicts a circuit diagram of the entire termite alarm unit in accordance with the present invention.

Referring next to FIG. 4, depicted is a circuit diagram for the sensor section 2 and the judgment section 15 including the alarm display section 16 and a counter 26. The sensor section 2, as described hereinbefore, includes the plurality of infrared rays emitting elements 7a and infrared rays receiving elements 7b, respectively four in this embodiment, arranged in parallel on the opposite ends of the through holes 6. Each infrared rays receiving element 7b transmits, based on the presence or absence of the obstruction of the infrared rays, a signal (in the form of a variation in voltage) to a logic circuit 24 of the judgment section 15. Whenever a termite is detected, the logic circuit 24 provides an output signal through a photo coupler 25 to the counter section 26.

The logic circuit 24 can employ, for example, a TTL (transistor-transistor logic) composed of 74LS32N (2-input OR gate) so as to provide an output signal when infrared rays to any one of the four infrared rays receiving elements 7b are obstructed by a termite.

The counter section 26 counts up the number of pulses sent out from the judgment section 15 for numerical display on the numerical displays 18.

Figure 5:
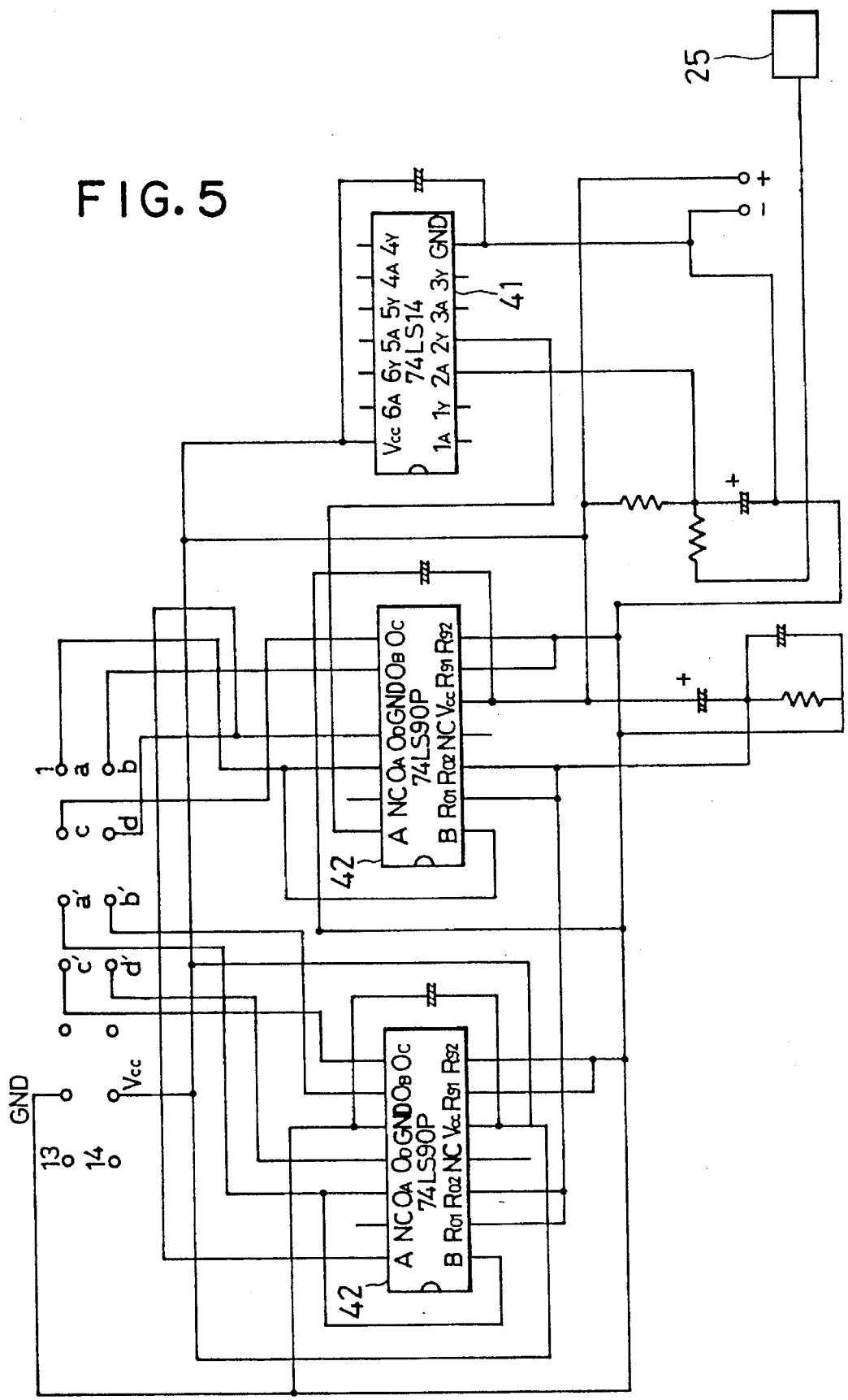
FIGS. 5 and 6 illustrate, by way of example, a configuration of a specific circuit of a counter section.
Figure 6:
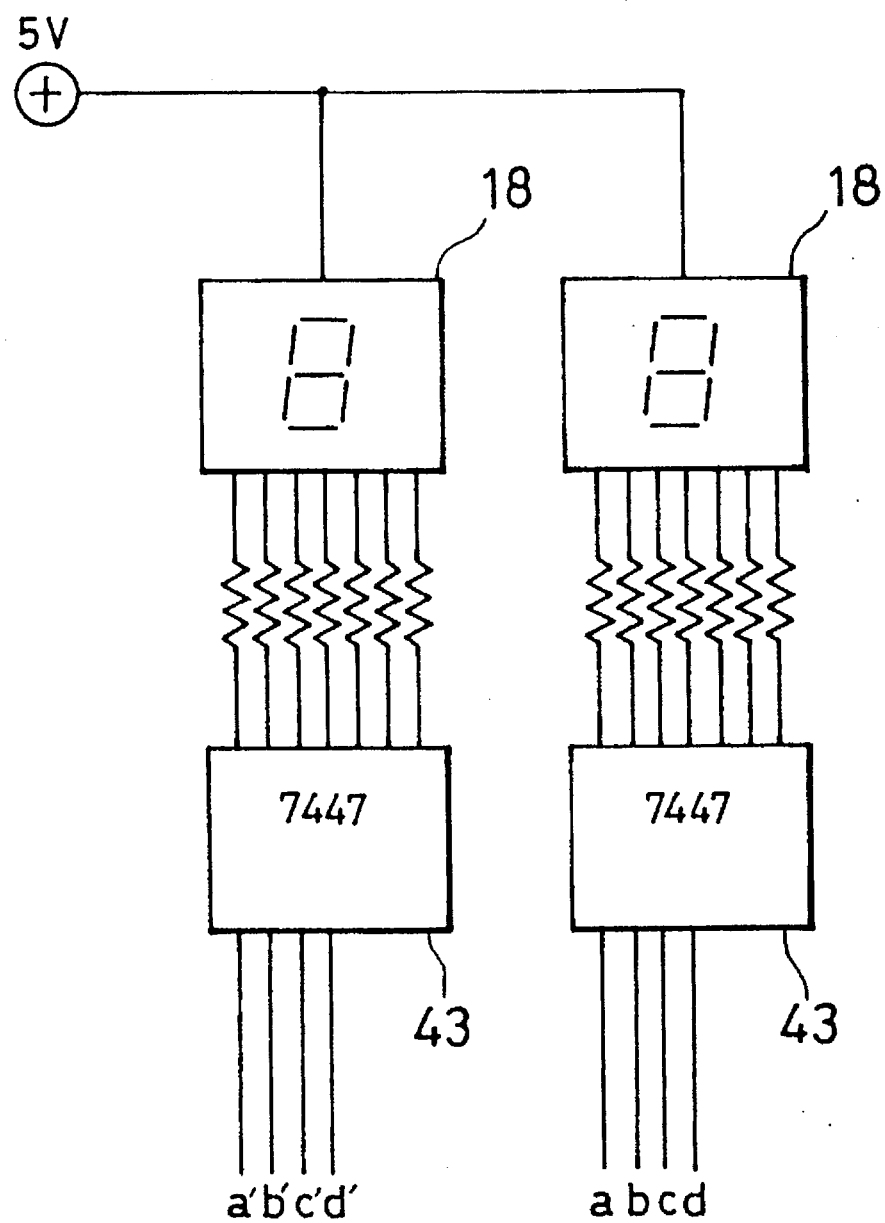

FIG. 5 depicts, by way of example, a specific configuration of the counter section 26 in which an inverter 41 composed of 74LS14 receives a signal transmitted via the photo coupler 25 from the logic circuit 24 and provides its output to a BCD counter consisting of two high-speed 4-bit ripple counters 42 each composed of 74LS90P. The ripple counters 42 have respective output terminals (a, b, c, d, and a',b', c', d') connected, for example, as shown in FIG. 6, to two decoders (BCD-to-Seven Segment Decoders) 43 each composed of 7447, thereby allowing a signal to be transmitted via the decoders 43 to the numerical displays 18 each composed of 7-segment LED's.

Upon the detection of a termite by the judgment section 15, the blue lamp 20 of the alarm display section 16 goes out and instead the red lamp 21 lights up for the display of an alarm. Although in this embodiment the alarm display section 16 receives a signal from the counter section 26, if the latter is not required, the former may directly receive a detection signal from the judgment section 15. Also, the infrared rays emitting elements and the infrared rays receiving elements used in pairs as sensors for detecting the termites may be substituted by pairs of ultrasonic waves emitting elements and ultrasonic waves receiving elements or other known transmitting and receiving element pairs. Further, the alarm display section 16 may include not only the display lamps but also known audible means such as buzzers.

What is claimed is:

1. A termite alarm unit comprising:

a sensor section including (a) a cellulose-containing member having a bottom surface and opposite side surfaces, said cellulose-containing member further having a plurality of vertical holes, each of said vertical holes extending vertically within said cellulose-containing member and having an opening at the bottom surface of said cellulose-containing member, and said cellulose-containing member further having a plurality of through holes, each of said through holes extending between the opposite side surfaces of said cellulose-containing member so as to cross and communicate with at least one of said vertical holes, (b) emitting elements, each of said emitting elements being inserted into one side of a respective one of said through holes and emitting an output wave, and (c) receiving elements, each of said receiving elements being inserted into another side of a respective one of said through holes and receiving the output wave emitted by a respective one of said emitting elements;

a judgement section generating an output signal upon detecting the invasion of termites in response to the obstruction of at least one output wave from said emitting elements to said receiving elements within said through holes; and an alarm display section for issuing an alarm in response to the output signal from said judgement section.

2. A termite alarm unit according to claim 1, further comprises:

a cover enclosing said cellulose-containing member and having an opening in a bottom thereof.

3. A termite alarm unit according to claim 1, wherein said cellulose-containing member is a lumber.

4. A termite alarm unit according to claim 1, wherein said cellulose-containing member is a hardened pulp.

5. A termite alarm unit according to claim 1, wherein said cellulose-containing member further includes a plurality of legs held in the ground.

6. A termite alarm unit according to claim 1, wherein each of said emitting elements is an infrared ray emitting element, and each of said receiving elements is an infrared ray receiving element.

7. A termite alarm unit according to claim 1, wherein each of said emitting elements is an ultrasonic wave emitting element, and each of said receiving elements is an ultrasonic wave receiving element.

8. A termite alarm unit according to claim 1, wherein said alarm display section further includes a counter which counts said output signal from said judgement section, said alarm display section issuing an alarm corresponding to a count number of said counter.

9. A termite alarm unit according to claim 8, wherein said alarm section issues an alarm whenever said counter counts to a present number.

10. A termite alarm unit comprising:

a sensor section including (a) a cellulose-containing member having a bottom surface and opposite side surfaces, said cellulose-containing member further having a plurality of vertical holes, each of said vertical holes extending vertically within said cellulose-containing member and having an opening at the bottom surface of said cellulose-containing member, and said cellulose-containing member further having a plurality of through holes, each of said through holes extending between the opposite side surfaces of said cellulose-containing member so as to cross and communicate with at least one of said vertical holes, (b) emitting elements, each of said emitting elements being inserted into one side of a respective one of said through holes and emitting an output wave, and (c) receiving elements, each of said receiving elements being inserted into another side of a respective one of said through holes and receiving the output wave emitted by a respective one of said emitting elements;

a judgement section generating an output signal upon detecting the invasion of termites in response to the obstruction of at least one output wave from said emitting elements to said receiving elements and said through holes; and an alarm display section including a counter which counts said output signal from said judgement section and issues an alarm corresponding to a count number of said counter; and a cover enclosing said cellulose-containing member and having an opening in a bottom thereof.

11. A termite alarm unit according to claim 10, wherein each of said emitting elements is an infrared ray emitting element, and each of said receiving elements is an infrared ray receiving element.

12. A termite alarm unit according to claim 10, wherein each of said emitting elements is an ultrasonic wave emitting element, and each of said receiving elements is an ultrasonic wave receiving element.

13. A termite alarm unit comprising:

a sensor section including (a) a cellulose-containing member having a bottom surface and opposite side surfaces, said cellulose-containing member further having a plurality of vertical holes, each of said vertical holes extending vertically within said cellulose-containing member and having an opening at the bottom surface of said cellulose-containing member, and said cellulose-containing member further having a plurality of through holes, each of said through holes extending between the opposite side surfaces of said cellulose-containing member so as to cross and communicate with at least one of said vertical holes, (b) emitting elements, each of said emitting elements being inserted into one side of a respective one of said through holes and emitting an output wave, and (c) receiving elements, each of said receiving elements being inserted into another side of a respective one of said through holes and receiving the output wave emitted by a respective one of said emitting elements;

a judgement section generating an output signal upon detecting the invasion of termites in response to the obstruction of at least one output wave from said emitting elements to said receiving elements and said through holes; and an alarm display section including a counter which counts said output signal from said judgement section and issues an alarm corresponding to a count number of said counter; and a cover enclosing said cellulose-containing member and having an opening in a bottom thereof; and a plurality of legs holding said cellulose-containing member in the ground.

14. A termite alarm unit according to claim 13, wherein each of said emitting elements is an infrared ray emitting element, and each of said receiving elements is an infrared ray receiving element.

15. A termite alarm unit according to claim 13, wherein each of said emitting elements is an ultrasonic wave emitting element, and each of said receiving elements is an ultrasonic wave receiving element.

\* \* \* \* \*